United States Patent
Kiani et al.

(10) Patent No.: US 8,547,209 B2
(45) Date of Patent: *Oct. 1, 2013

(54) ALARM SUSPEND SYSTEM

(75) Inventors: Massi Joe E. Kiani, Laguna Niguel, CA (US); Steve L. Cebada, Mission Viejo, CA (US); Gregory A. Olsen, Trabuco Canyon, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,725

(22) Filed: May 21, 2012

(65) Prior Publication Data

US 2012/0232366 A1 Sep. 13, 2012

Related U.S. Application Data

(63) Continuation of application No. 12/510,982, filed on Jul. 28, 2009, now Pat. No. 8,203,438.

(60) Provisional application No. 61/084,615, filed on Jul. 29, 2008.

(51) Int. Cl.
*G08B 5/22* (2006.01)

(52) U.S. Cl.
USPC .............. 340/286.07; 340/539.12; 340/573.1; 600/322; 600/323; 600/324

(58) Field of Classification Search
USPC ............ 340/511, 517, 573.1, 539.12, 286.07, 340/527; 128/905; 600/310, 316, 322–324, 600/336, 344, 507, 301, 320
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |

(Continued)

*Primary Examiner* — Brent Swarthout
(74) *Attorney, Agent, or Firm* — Knobbe Martens Olson & Bear, LLP

(57) ABSTRACT

An alarm suspend system utilizes an alarm trigger responsive to physiological parameters and corresponding limits on those parameters. The parameters are associated with both fast and slow treatment times corresponding to length of time it takes for a person to respond to medical treatment for out-of-limit parameter measurements. Audible and visual alarms respond to the alarm trigger. An alarm silence button is pressed to silence the audible alarm for a predetermined suspend time. The audible alarm is activated after the suspend time has lapsed. Longer suspend times are associated with slow treatment parameters and shorter suspend times are associated with fast treatment parameters.

23 Claims, 5 Drawing Sheets

(56) References Cited

U.S. PATENT DOCUMENTS

| | | |
|---|---|---|
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 * | 12/2003 | Kianl et al. .................. 600/322 |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |

| | | |
|---|---|---|
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,203,438 B2 * | 6/2012 | Kiani et al. ............... 340/286.07 |
| 2007/0040692 A1 * | 2/2007 | Smith et al. ................ 340/573.1 |
| 2008/0244425 A1 * | 10/2008 | Kikin-Gil et al. ............. 715/764 |
| 2010/0331656 A1 | 12/2010 | Mensinger et al. |

* cited by examiner

200

ALARM SUSPEND SYSTEM

CROSS-REFERENCE TO RELATED APPLICATIONS

This application is a continuation of U.S. patent application Ser. No. 12/510,982 filed Jul. 28, 2009, now U.S. Pat. No. 8,203,438 and entitled "Alarm Suspend System," which claims priority benefit under 35 U.S.C. §119(e) to U.S. Provisional Patent Application Ser. No. 61/084,615, filed Jul. 29, 2008, titled "Alarm Management System." All of the above referenced applications are hereby incorporated by reference in their entirety herein.

BACKGROUND

Pulse oximetry for measuring constituents of circulating blood has achieved acceptance in a wide variety of medical applications, including surgical wards, intensive care and neonatal units, general wards, home care, physical training, and virtually all types of monitoring scenarios. A pulse oximeter generally includes a two-wavelength optical sensor applied to a patient, a monitor for processing sensor signals and displaying results and a patient cable electrically interconnecting the sensor and the monitor. The monitor typically provides a numerical readout of physiological parameters such as oxygen saturation ($SpO_2$) and pulse rate (PR). Advanced physiological monitors utilize multiple wavelength sensors and enhanced measurement capabilities to provide readouts of additional parameters, such as carboxyhemoglobin (HbCO), methemoglobin (HbMet) and total hemoglobin (Hbt).

Pulse oximeters capable of reading through motion induced noise are disclosed in at least U.S. Pat. Nos. 6,770,028, 6,658,276, 6,650,917, 6,157,850, 6,002,952, 5,769,785 and 5,758,644; low noise pulse oximetry sensors are disclosed in at least U.S. Pat. Nos. 6,088,607 and 5,782,757; all of which are assigned to Masimo Corporation, Irvine, Calif. ("Masimo") and are incorporated by reference herein.

Physiological monitors and corresponding multiple wavelength optical sensors are described in at least U.S. patent application Ser. No. 11/367,013, filed Mar. 1, 2006 and titled Multiple Wavelength Sensor Emitters and U.S. patent application Ser. No. 11/366,208, filed Mar. 1, 2006 and titled Noninvasive Multi-Parameter Patient Monitor, both assigned to Masimo Laboratories, Irvine, Calif. (Masimo Labs) and both incorporated by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and RAD-57™ and Radical-7™ monitors for measuring $SpO_2$, pulse rate (PR), perfusion index (PI), pleth variability index (PVI), signal quality, HbCO and HbMet among other parameters are also available from Masimo.

SUMMARY OF THE INVENTION

Monitor alarms are triggered by out-of-limit parameters and system failures, the latter including monitor or sensor failures or improper sensor placement, to name a few. Alarms can be visual, audible or both. Alarms can also have different levels of priority, which are reflected in the type of visual and audible alarms. In an embodiment, parameters exceeding limits such as low $SpO_2$, high HbCO, high HbMet and low and high BPM trigger high priority alarms. System failures due to sensor off, no sensor or defective sensor also trigger high priority alarms. Parameters exceeding limits such as high $SpO_2$, low and high PI, low and high PVI, for example, trigger medium priority alarms. Parameters exceeding limits such as low HbCO and low HbMet along with a system low battery indication are examples of low priority alarms.

An audible alarm may be temporarily suspended by pressing an alarm silence button so as to prevent unnecessary disturbance to the patient and distraction of the caregiver. During alarm suspension, visual alarms remain active. If an alarm condition persists after a predetermined alarm suspend period, the audible alarm resumes. The alarm suspend period is typically long enough to give a caregiver sufficient time to intervene with appropriate patient treatment yet short enough to ensure that patient health is not endangered if intervention is ineffective. For conventional pulse oximetry, an alarm suspend may be, for example, a maximum of 120 seconds.

Alarm suspension on advanced blood parameter monitors is problematic. With conventional pulse oximetry, treatment for abnormal parameter measurements can be quickly applied and a patient response is typically fast. For example, a treatment for low oxygen saturation is the application of an oxygen mask or an increase in oxygen flow. By contrast, the duration of treatment for parameters measured by advanced monitors is highly dependent on the alarm-triggering parameter. For example, the treatment for high methemoglobin is the injection of methylene blue, and the patient response to such an injection is slow. When patient treatment time exceeds the maximum alarm suspend period, an audible alarm will constantly reactivate. Thus, a single alarm suspend duration for all parameters is inadequate to cope with the many different types of parameters measured by advanced monitors.

One aspect of an alarm suspend system for silencing the alarms is an alarm trigger responsive to any of various parameters and predetermined limits corresponding to the parameters, where the parameters are partitioned according to treatment time, i.e. the relative length of time it takes for a person to respond to medical treatment for a parameter measurement outside of the predetermined limits. An audible alarm is responsive to the alarm trigger. An alarm silence button is actuated so as to suspend the audible alarm. A timer tracks the duration of the suspended alarm and is initiated by actuation of an alarm silence button. The timer retriggers the audible alarm after the timed duration has lapsed/expired. In an embodiment, a long duration suspend time is associated with slow treatment parameters and a short duration suspend time is associated with fast treatment parameters. Fast treatment parameters may include, for example, parameters relating to normal blood hemoglobin constituents and slow treatment parameters may include parameters relating to abnormal blood hemoglobin constituents.

In various embodiments, a short duration suspend time is less than or equal to about two minutes and a long duration suspended time is greater than about two minutes. A default duration associated with the fast treatment parameters is about two minutes and a default duration associated with the slow treatment parameters is about fifteen minutes. The alarm suspend system may also have an alarm suspend override responsive to a predetermined unit change in the parameter triggering a suspended alarm. The override results in reactivation of the suspended alarm. A physiological monitor having an alarm suspend system may also have a pop-up window that appears on the monitor display in response to actuation of the silence button, where the pop-up window presents a choice of alarm suspend durations.

Another aspect of an alarm suspend system is a partition of measured parameters into at least a first group and a second group. An audible alarm is triggered if at least one parameter is outside of predetermined limits. The audible alarm is suspended in response to a silence request. A first duration is associated with the first group and a second duration is associated with the second group. The audible alarm is reactivated after at least one of the first duration and the second duration. The first duration may be set so as to generally correspond to a first range of treatment times for the first group of parameters. Likewise, the second duration may be set so as to generally correspond to a second range of treatment times for the second group of parameters, where the first range of treatment times and the second range of treatment times are non-overlapping.

In various embodiments, suspended audible alarms are overridden if the triggering parameter has greater than a predetermined unit change before the suspended alarm expires according to either the first duration or the second duration. The first and second groups are defined in relation to normal hemoglobin measurements abnormal hemoglobin measurements, respectively. The first duration is set to be less than or equal to two minutes and the second duration is set to be greater than two minutes, with default durations of about two minutes corresponding to the first group and about fifteen minutes corresponding to the second group. In an embodiment, a pop-up window for a monitor display is constructed and the first duration and the second duration are selected from a range of durations presented within the pop-up window.

A further aspect of an alarm suspend system deactivates an audible alarm for one of a short duration and a long duration according to the alarm-triggering parameter. A first group of parameters is associated with the short duration and a second group of parameters is associated with the long duration. The first group and the second group are partitioned according to a fast treatment time and a short treatment time associated with the parameters. An override reactivates the audible alarm if the trigger parameter changes more than a predetermine amount during the corresponding duration. In various embodiments, the first group comprises parameters related to the measurement of normal hemoglobin and the second group comprises parameters related to the measurement of abnormal hemoglobin. The long duration is greater than about 120 seconds and the short duration is less than or equal to about 120 seconds. A pop-up window for the display allows selection of the long duration and the short duration in response to the silence button.

DETAILED DESCRIPTION

Figure 1:
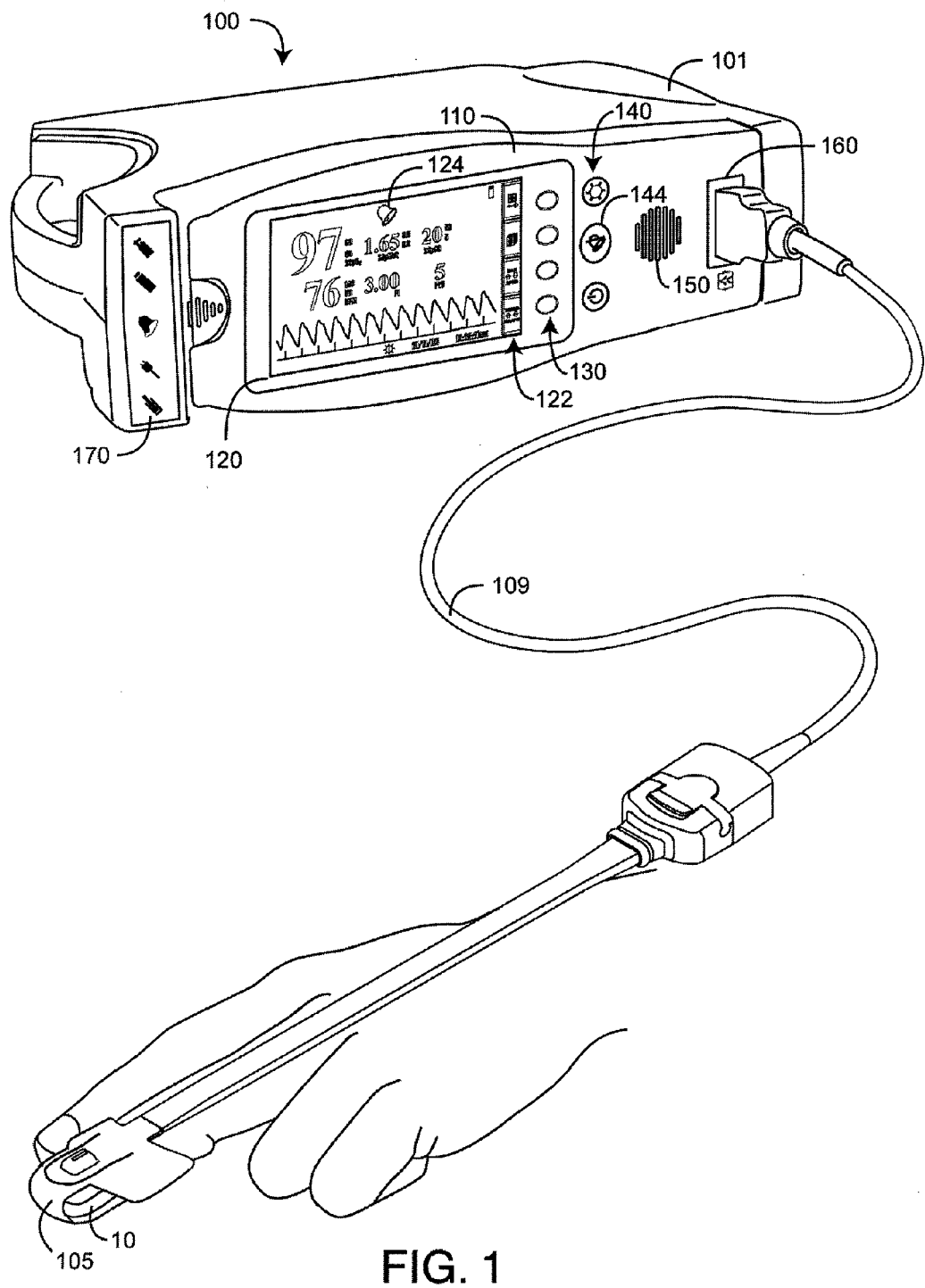
FIG. 1 is a perspective view of a physiological measurement system utilizing an alarm suspend system.

FIG. 1 illustrates a physiological measurement system 100 that utilizes an alarm suspend system. The physiological measurement system 100 has a noninvasive sensor 105 attached to a tissue site 10, a physiological monitor 101, and an interface cable 109 interconnecting the monitor 101 and the sensor 105. The physiological measurement system 100 may incorporate pulse oximetry in addition to advanced features, such as a multiple wavelength sensor and advanced processes for determining physiological parameters other than or in addition to those of pulse oximetry, such as carboxyhemoglobin, methemoglobin and total hemoglobin, as a few examples.

The monitor 101 has a front panel 110 providing a display 120, touch keys 130, controls 140, a speaker 150, a sensor port 160 and status indicators 170. The display 120 shows parameter readouts, limits and waveforms among other items. The display 120 also has touch key icons 122 that indicate touch key 130 functions. The speaker 150 provides an audible alarm in response to physiological measurements that violate preset conditions, such as an out-of-limit parameter, as well as system failures, such as a low battery condition. The controls 140 include an alarm silence button 144 that is pressed to temporarily suspend out-of-limit parameter alarms and system alarms, such as low battery. The display 120 provides visual alarms, which include a bell-shaped alarm status indicator 124 that illuminates during an alarm condition and parameter readouts 210 and limits 220 that flash when parameters are out-of-limit. Status indicators 170 also provide visual alarms. When there are multiple alarm conditions, the parameter displays 202 indicate parameters with the highest alarm priority. Touch keys 130 and corresponding icons 122 include an alarm menu access button for setting alarm conditions, such as high or low alarm limits for $SpO_2$, HbCO, HbMet, PR and PI. The alarm silence button 144 is pressed to temporarily suspend audible alarms. Advantageously, an alarm suspend system provides a parameter-dependent variation in the alarm suspend duration, as described below, utilizing a common silence button or other suspend initiator.

Figure 2:
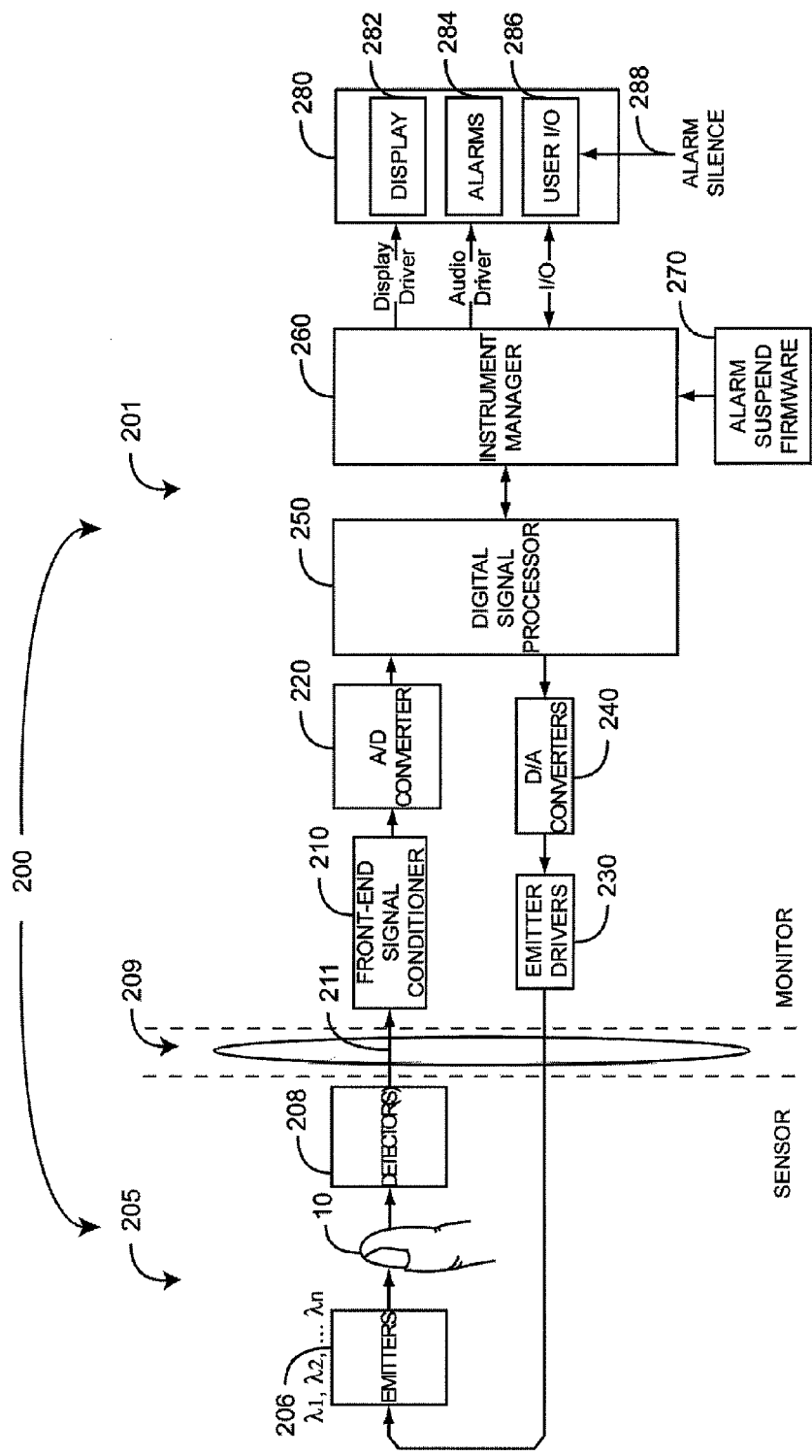
FIG. 2 is a detailed block diagram of a physiological measurement system utilizing an alarm suspend system.

FIG. 2 illustrates a physiological measurement system 200 including a physiological monitor 201, a sensor 205 and an interface cable 209. The sensor 205 is attached to a tissue site, such as a finger 10, and includes a plurality of emitters 206 irradiating the tissue site 10 with multiple wavelengths of light. The sensor 205 also includes one or more detectors 208 capable of detecting the light after attenuation by the tissue site 10. The sensor 205 transmits optical radiation at wavelengths other than or including the red and infrared wavelengths utilized in pulse oximeters. The monitor 201 inputs a corresponding sensor signal 211 and determines the relative concentrations of blood constituents other than or in addition to the "normal" blood hemoglobin constituents $HbO_2$ and Hb, including "abnormal" blood hemoglobin constituents HbCO, HbMet and blood related parameters such as fractional oxygen saturation, total hemoglobin and blood glucose to name a few.

As shown in FIG. 2, the monitor 201 has a front-end signal conditioner 210, an ND converter 220, emitter drivers 230, D/A converters 240 and a digital signal processor ("DSP") 250. In general, the emitter drivers 230 convert digital control signals, via the D/A converters 240, into analog drive signals capable of driving the sensor emitters 206. The front-end signal conditioner 210 converts, via the ND converter 220, composite analog intensity signal(s) from light sensitive detector(s) 208 into digital data input to the DSP 250. The emitter drivers 230 and front-end signal conditioner 210 communicate with the sensor 205 via the interface cable 209.

Also shown in FIG. 2, the monitor 201 has an instrument manager 260 and a user interface 280. The user interface 280 includes one or more displays 282, alarms 284 and user input/output (I/O) 286. The instrument manager 260 communicates with the DSP 250 to receive parameter data and to present that data on the display 282. The instrument manager 260 may also store and display historical or trending data related to one or more of the measured parameters or combinations of the measured parameters. The instrument manager 260 also controls audible and visual alarms and indicators 284. The instrument manager 260 responds to user-actuated keys and communicates with external devices via various I/O ports 286. Further, the instrument manager 260 executes alarm suspend firmware 270 so as to respond to an alarm silence button press 288, as described in detail with respect to FIGS. 3-4.

Figure 3:
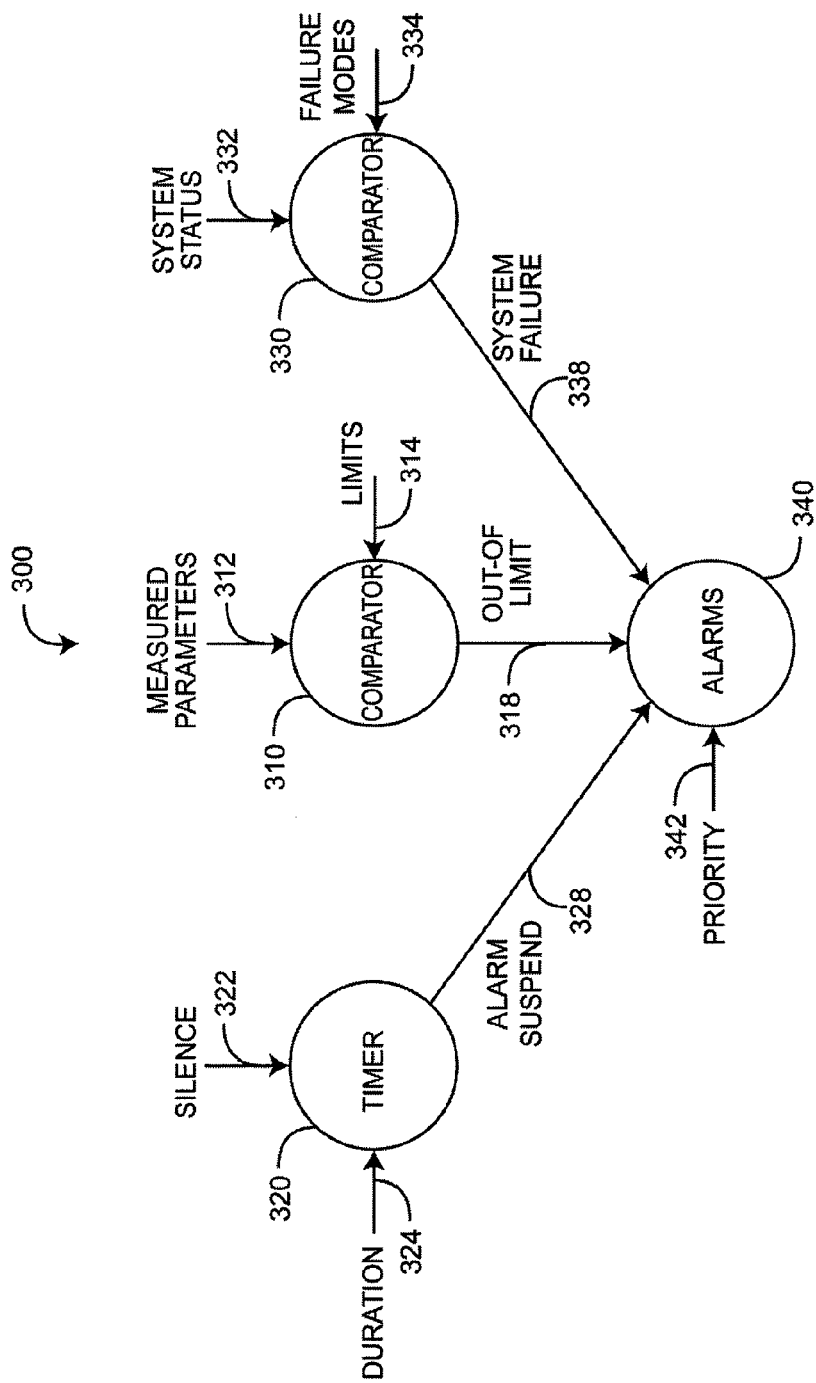
FIG. 3 is a flow diagram of an alarm suspend system embodiment.

FIG. 3 generally illustrates an alarm suspend system 300. Alarm triggers include system failures 338 and out-of-limit parameters 318. Triggered alarms 340 may be audible, visual or both, and may vary according to priority 342. Audible alarms may be generated by a monitor front-panel-mounted speaker 150 (FIG. 1) and may vary in loudness, pitch and sound pattern. Visual alarms may include parameter labels, parameter numerics, symbols and status lights, which can flash and vary in color.

As shown in FIG. 3, measured parameters 312 are compared 310 to default or user-specified limits 314. An out-of-limit condition 318 triggers an alarm 340. An alarm suspend 328 is user-initiated by a silence request 322. This may be a press of a silence button 144 (FIG. 1) on a monitor front panel 110 (FIG. 1). In an embodiment, the alarm suspend 328 silences audible alarms and modifies the display of visual alarms. The alarm suspend 328 is based on a timer 320, which ends the alarm suspend 328 after a predetermined duration 324. The duration 324 may be a function of the out-of-limit parameter 312. In an advantageous embodiment, the duration 324 relates to, or is a function of, the treatment time for the alarm-triggering parameter so as to avoid nuisance alarms while maintaining alarm integrity.

Figure 4:
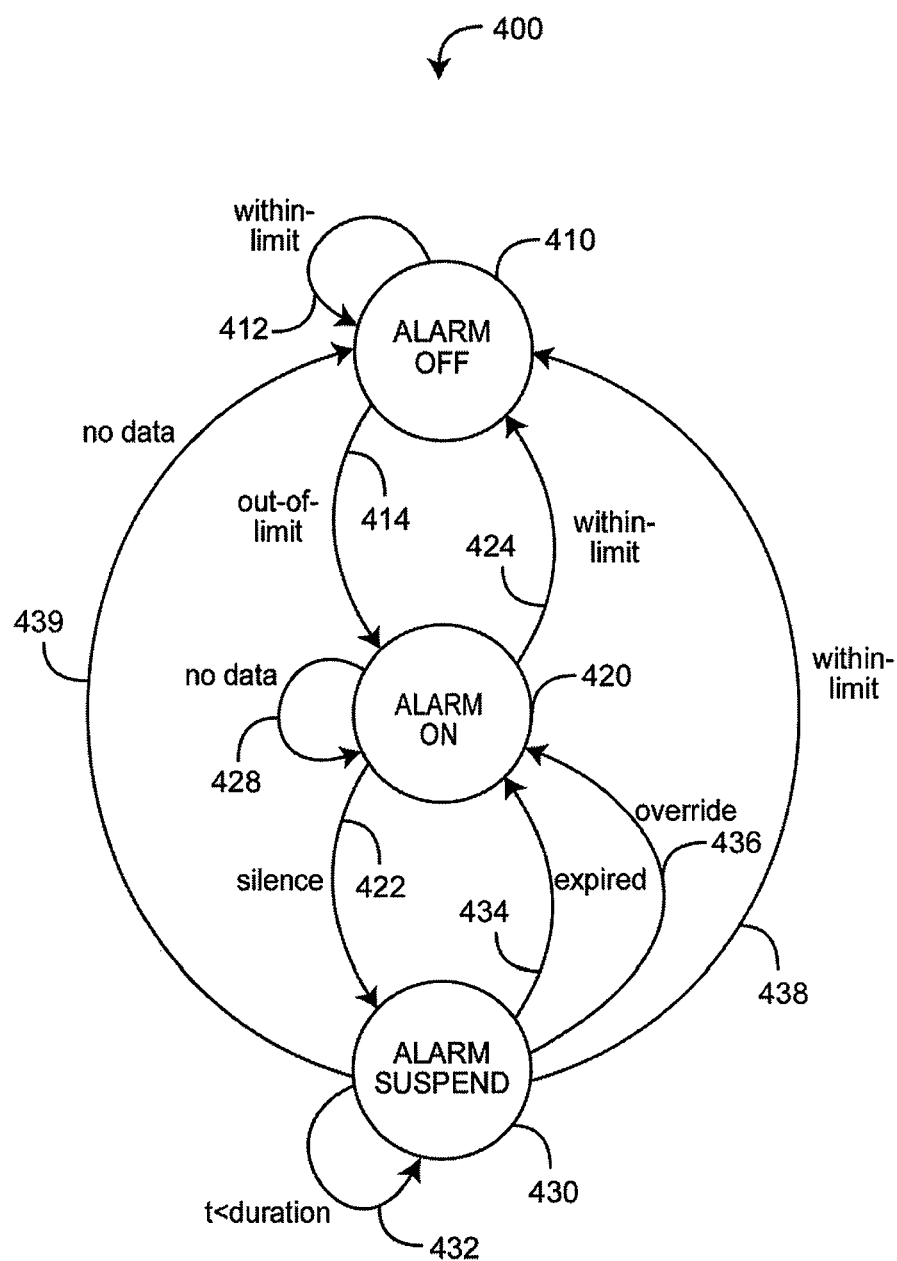
FIG. 4 is a state diagram of an alarm suspend system embodiment.

FIG. 4 illustrates an alarm suspend embodiment 400 that operates independently for each measured parameter that can trigger an alarm. An alarm is initially off 410. The alarm remains off as long as the parameter is within its set limits 412. If a parameter is measured outside of its set limits 414, an alarm is triggered 420. The alarm may audible, visual or both audible and visual. A user can request to silence the alarm by pressing an alarm silence button 144 (FIG. 1), for example. The silence request 422 suspends the alarm 430 which turns off audible alarms but, in an embodiment, does not deactivate visual alarms. The audible alarm remains suspended 430 for a predetermined duration 432. When the suspend duration has passed, the alarm suspend expires 434 and audible alarms are once again activated 420. The alarm remains on 428 until the triggering parameter is within limits 424 or a user once again requests silence 422. The alarm suspend 430 deactivates if the measured parameter becomes within limits 438, such as when the patient condition improves, or if no physiological data is detected 439, such as no sensor, sensor off, no cable or malfunctioning sensor situations, to name a few. Also, if the measured parameter changes during the alarm suspend 430 by a sufficient out-of-limit amount, an override 436 reactivates the audible alarms 420.

In an alarm suspend system embodiment, parameters are classified according to the typical time it takes for medical treatment to transition an out-of-limit measurement to a within-limit measurement. Suspend durations 324 (FIG. 3) are set accordingly. For example, in a two-tier embodiment, relatively slow treatment parameters, such as HbMet, HbCO, Hbt and PVI, are assigned relatively long suspend durations. Similarly, relatively fast treatment parameters, such as SpO$_2$ and PR, are assigned relatively short suspend durations. In an embodiment, the alarm suspend duration is adjustable for each individual parameter, including 2, 5, 10, 15, 20, 25 and 30 minutes for slow treatment parameters, with a default of 15 minutes; and 30, 60, 90 and 120 seconds for fast treatment parameters, with a default of 120 seconds. These alarm features are only active when alarm limits have been set. Other alarm features apply to both slow treatment and fast treatment parameters. For example, an alarm delay of 0, 5, 10 or 15 seconds applies to all enabled parameters.

In an embodiment, an override 436 occurs if slow treatment parameters such as HbCO, HbMet or PVI increase or Hbt decreases by a certain unit change during the alarm suspend duration. The unit change is adjustable for each parameter, such as from 1-15 in increments of 1. TABLE 1 shows a default embodiment of override unit changes for these parameters.

TABLE 1

| Override Unit Changes for Selected Parameters | | |
|---|---|---|
| Parameter | Unit Change | Direction |
| HbCO | 5 | Increase |
| HbMet | 2 | Increase |
| Hbt | 2 | Decrease |
| PVI | OFF | Increase |

Figure 5:
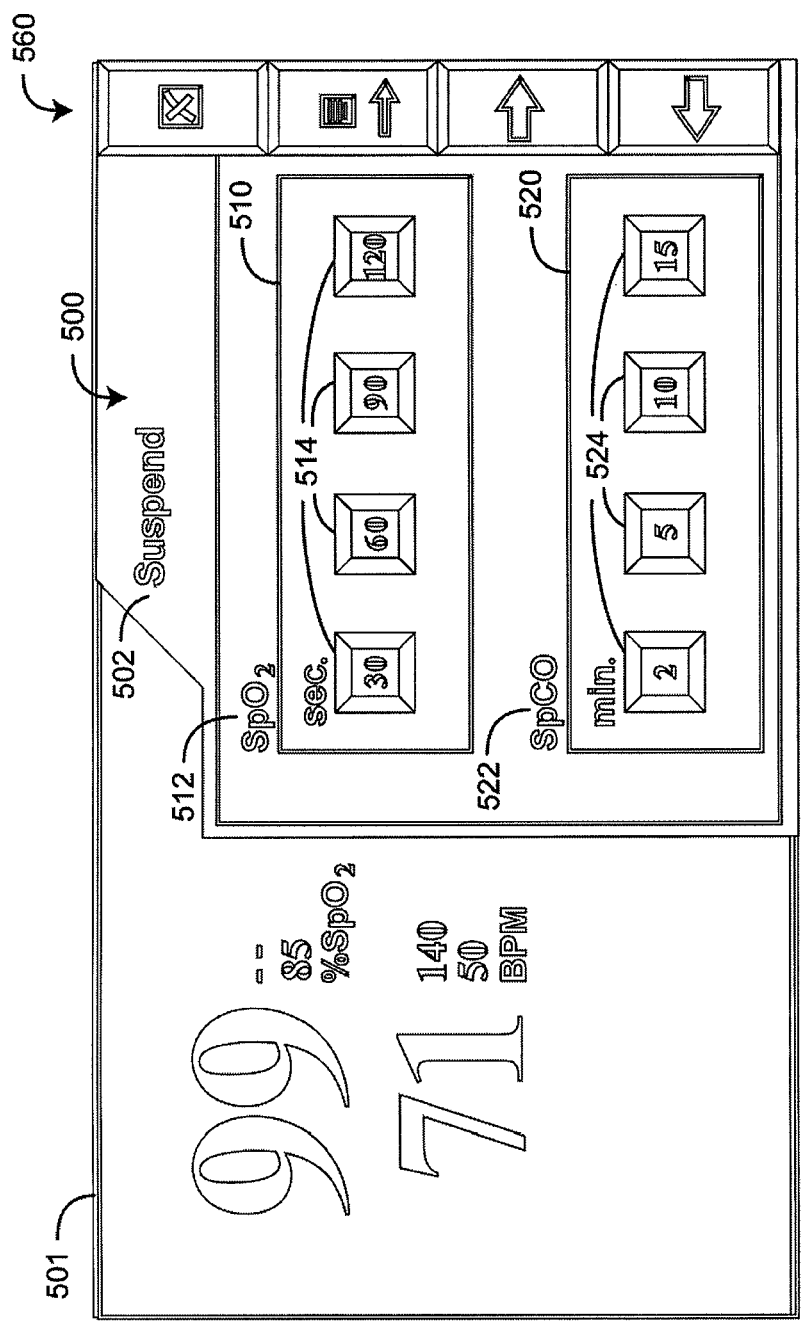
FIG. 5 is an illustration of an alarm suspend pop-up window.

FIG. 5 illustrates an alarm suspend window 500 that provides a "pop-up" display so that a monitor user may manually enter an alarm suspend duration. The alarm suspend window 500 appears as a portion of a monitor display 501, such as the front panel display 120 (FIG. 1) described above. The pop-up window 500 responds to a suspend request, such as a silence button 144 (FIG. 1) press. The alarm suspend window 500 has a window identifier 502 and one or more parameter subsections 510, 520. Each parameter subsection 510, 520 has a parameter identifier 512, 522 and corresponding suspend duration options 514, 524. In an embodiment, specific suspend times are selected via monitor touch keys 130 (FIG. 1) as guided by corresponding touch key icons 560. Selected suspend times are highlighted or otherwise identified and entered, also via a touch key 130 (FIG. 1). In an alternative embodiment, the monitor display is a touch screen and alarm suspend times are directly entered by a finger press on a specific duration "virtual button" 514, 524. Once one or more suspend durations are entered, the pop-up window 500 disappears from the display 501. The alarm suspend window 500 advantageously allows a user to quickly choose an appropriate alarm suspend duration for the situation at hand, rather than relying on a predetermined or default duration.

An alarm suspend system is described above with respect to alarms triggered by measured parameters and limits associated with those measured parameters. Limits may correspond to levels of a measured parameter, such as a percentage oxygen saturation to name but one example. Limits may also correspond to trends of a measured parameter, such as a rate-of-change of oxygen saturation, for example. Limits may also correspond to patterns in a measured parameter or a comparison of one measured parameter with another measured parameter, as further examples.

An alarm suspend system is described above with respect to a two-tier grouping of parameters, such as slow treatment and fast treatment parameters and alarm suspend durations associated with those groups. Groupings of parameters with respect to alarm suspend durations may be multi-tier, such as slow, medium and fast treatment parameters, to name but one example.

An alarm suspend system has been disclosed in detail in connection with various embodiments. These embodiments are disclosed by way of examples only and are not to limit the scope of the claims that follow. One of ordinary skill in the art will appreciate many variations and modifications.

What is claimed is:

1. A noninvasive optical based physiological measurement system comprising:
a plurality of light emitting diodes configured to transmit a plurality of wavelengths of light onto a tissue site of a patient;
at least one detector configured to measure an indication of the plurality of wavelengths of light after attenuation by tissue of the patient and output a signal indicative of the attenuated light;
one or more processors configured to receive the detector output signal and to determine a plurality of different physiological measurements, the one or more processors further configured to determine if an alarm threshold has been met and activate an alarm;
a speaker associated with the one or more processors, the speaker configured to generate an audible signal in response to the alarm activated by the one or more processors; and
a silence button associated with the one or more processors,
wherein, when the alarm is activated for at least one of the plurality of different physiological measurements and the silence button is activated by a user, the one or more processors deactivate the alarm for a period of time, the period of time being different for each different physiological measurement of the plurality of different physiological measurements.

2. The noninvasive optical based physiological measurement system of claim 1, wherein the physiological measurements comprise one or more of oxygen saturation, pulse rate, carboxyhemoglobin, methemoglobin and total hemoglobin.

3. The noninvasive optical based physiological measurement system of claim 1, wherein the period of time is related to an expected course of treatment for the activated alarm.

4. An alarm suspend method comprising:
measuring at least two physiological parameters using a patient monitoring device including a processor and a memory device configured to store parameter specific alarm suspension periods of time, wherein a different alarm suspension period of time is associated with each of the at least two physiological parameters;
triggering an audible alarm if at least one physiological parameter is outside of predetermined limits;
suspending the audible alarm temporarily in response to a silence request; and
reactivating the audible alarm after the alarm suspension period of time associated with the at least one physiological parameter outside the predetermined limits has passed.

5. The alarm suspend method according to claim 4, further comprising setting the alarm suspension period of time to correspond with a range of treatment times associated with each of the at least two physiological parameters.

6. The alarm suspend method according to claim 4, further comprising overriding the suspended audible alarm if the triggering parameter has greater than a predetermined unit change before the alarm suspension period of time has passed.

7. The alarm suspend method according to claim 4, wherein at least one alarm suspension period of time is about two minutes.

8. The alarm suspend method according to claim 4, wherein at least one alarm suspension period of time is about fifteen minutes.

9. The alarm suspend method according to claim 4, further comprising:
constructing a pop-up window for a monitor display; and
selecting the alarm suspension period of time from a range of alarm suspension periods of time presented within the pop-up window.

10. The alarm suspend method according to claim 4, further comprising triggering the audible alarm if no parameters are found during measuring.

11. The alarm suspend method according to claim 4, wherein the plurality of physiological parameters are measured using multiple wavelength sensing.

12. The alarm suspend method according to claim 6, wherein the predetermined unit change is adjustable for each physiological parameter.

13. A physiological measurement system comprising:
a sensor configured to attach to a patient so as to transmit optical radiation into a tissue site and generate a sensor signal responsive to the optical radiation after attenuation by pulsatile blood flow within the tissue site;
a monitor in communications with the sensor so as to measure a plurality of physiological parameters responsive to the sensor signal;
a display mounted on the monitor that displays the measured physiological parameters along with visual alarms associated with the measured physiological parameters;
a speaker mounted on the monitor that generates an audible alarm triggered by at least one of the physiological parameters;
a silence button mounted on the monitor that, when actuated, initiates a silence request for the monitor to suspend the audible alarm; and
an alarm suspend system that deactivates the audible alarm for a parameter specific duration according to the alarm-triggering parameter, wherein the parameter specific duration is different for at least two of the physiological parameters.

14. The physiological measurement system according to claim 13, wherein the alarm suspend system comprises:
a first group of parameters associated with a short duration;
a second group of parameters associated with a long duration;
the first group and the second group partitioned according to a fast treatment time and a short treatment time associated with the parameters.

15. The physiological measurement system according to claim 13, further comprising an override that reactivates the audible alarm if the triggered parameter changes more than a predetermine amount during the corresponding duration.

16. The physiological measurement system according to claim 14, wherein the first group comprises parameters related to the measurement of normal hemoglobin and the second group comprises parameters related to the measurement of abnormal hemoglobin.

17. The physiological measurement system according to claim 14, wherein the long duration is greater than about 120 seconds.

18. The physiological measurement system according to claim 14, wherein the short duration is less than or equal to about 120 seconds.

19. The physiological measurement system according to claim 14, further comprising a pop-up window for the display that allows selection of the long duration and the short duration in response to the silence button.

20. The physiological measurement system according to claim 14, further comprising:
  a third group of parameters associated with a high priority;
  a fourth group of parameters associated with a low priority;
  the third group and the fourth group partitioned according to a high medical priority and a low medical priority associated with the parameters; and
  wherein the visual alarms associated with the third group are displayed when both the visual alarms associated with the third group and the fourth group are to be displayed.

21. The physiological measurement system according to claim 13, wherein the parameter specific duration is the same for at least two of the physiological parameters.

22. The alarm suspend method according to claim 4, further comprising:
  transmitting, with a plurality of light emitting diodes, a plurality of wavelengths of light into a tissue site of a patient;
  detecting, with a light detector, the plurality of wavelengths of light after attenuation by tissue of the patient; and
  transmitting, from the detector to the patient monitor, an indication of the detected wavelengths of light,
  wherein the measuring is accomplished based at least in part on the indication of the detected wavelengths of light.

23. The alarm suspend method according to claim 4, further comprising:
  measuring at least one additional physiological parameter using the patient monitoring device including the processor and the memory device,
  wherein an alarm suspension period of time associated with the at least one additional physiological parameter is the same as the alarm suspension period of time associated with at least one of the at least two physiological parameters.

* * * * *

UNITED STATES PATENT AND TRADEMARK OFFICE
CERTIFICATE OF CORRECTION

PATENT NO. : 8,547,209 B2
APPLICATION NO. : 13/476725
DATED : October 1, 2013
INVENTOR(S) : Kiani et al.

It is certified that error appears in the above-identified patent and that said Letters Patent is hereby corrected as shown below:

In the Specification

In column 1 at line 45, Change "Multi- Parameter" to --Multi-Parameter--.

In column 4 at line 54, Change "ND" to --A/D--.

In column 4 at line 59, Change "ND" to --A/D--.

Signed and Sealed this
Twentieth Day of May, 2014

Michelle K. Lee
*Deputy Director of the United States Patent and Trademark Office*